(12) United States Patent
Yamashita

(10) Patent No.: US 9,603,520 B2
(45) Date of Patent: Mar. 28, 2017

(54) OPHTHALMIC APPARATUS, IMAGE PROCESSING METHOD, AND STORAGE MEDIUM

(71) Applicant: CANON KABUSHIKI KAISHA, Tokyo (JP)

(72) Inventor: Yutaka Yamashita, Shiroi (JP)

(73) Assignee: Canon Kabushiki Kaisha, Tokyo (JP)

( * ) Notice: Subject to any disclaimer, the term of this patent is extended or adjusted under 35 U.S.C. 154(b) by 466 days.

(21) Appl. No.: 14/068,357

(22) Filed: Oct. 31, 2013

(65) Prior Publication Data

US 2014/0132927 A1 May 15, 2014

(30) Foreign Application Priority Data

Nov. 9, 2012 (JP) ................. 2012-247751

(51) Int. Cl.
*A61B 3/14* (2006.01)
*A61B 3/15* (2006.01)
*A61B 3/00* (2006.01)

(52) U.S. Cl.
CPC .............. *A61B 3/14* (2013.01); *A61B 3/0025* (2013.01); *A61B 3/152* (2013.01)

(58) Field of Classification Search
CPC ..... A61B 3/0041; A61B 3/0075; A61B 3/117; A61B 3/14; A61B 3/15; A61B 3/152
USPC ................... 351/206, 208, 264, 210
See application file for complete search history.

(56) References Cited

U.S. PATENT DOCUMENTS

| | | | |
|---|---|---|---|
| 7,347,550 B2 | 3/2008 | Okinishi | |
| 7,354,154 B2 | 4/2008 | Matsumoto | |
| 7,566,130 B2 | 7/2009 | Okinishi | |
| 7,572,009 B2 | 8/2009 | Suzuki | |
| 7,780,292 B2 * | 8/2010 | Kakuuchi | A61B 3/12 351/206 |
| 7,896,494 B2 | 3/2011 | Inoue et al. | |
| 2005/0036111 A1 | 2/2005 | Okinishi | |
| 2005/0270485 A1 | 12/2005 | Matsumoto | |
| 2007/0132951 A1 | 6/2007 | Suzuki | |
| 2007/0273829 A1 | 11/2007 | Okinishi | |
| 2010/0157245 A1 | 6/2010 | Inoue et al. | |

(Continued)

FOREIGN PATENT DOCUMENTS

CN 1579320 A 2/2005
CN 1706341 A 12/2005

(Continued)

OTHER PUBLICATIONS

Jun. 3, 2015 Chinese Official Action in Chinese Patent Appln. No. 201310553117.8.

*Primary Examiner* — Huy K Mai
(74) *Attorney, Agent, or Firm* — Fitzpatrick, Cella, Harper & Scinto

(57) ABSTRACT

A ophthalmic apparatus includes: an imaging unit configured to obtain, through a photographing optical system, an image of an eye to be examined which is illuminated with illumination light from an observation light source of an illumination optical system; a display unit configured to display the image obtained by the imaging unit; and an image processing unit configured to display an image of the eye on the display unit at a display magnification corresponding to an observation portion of the eye or a display magnification corresponding to operation of the imaging unit.

33 Claims, 8 Drawing Sheets

| OBSERVATION MODE | DISPLAY MAGNIFICATION |
|---|---|
| ANTERIOR OCULAR OBSERVATION | ×2.0 |
| FUNDUS OBSERVATION | ×1.3 |
| ANTERIOR OCULAR IMAGING | ×1.0 |

(56) References Cited

U.S. PATENT DOCUMENTS

| | | | |
|---|---|---|---|
| 2011/0051089 A1* | 3/2011 | Wada | A61B 3/12 351/208 |
| 2012/0237108 A1 | 9/2012 | Yamashita | |

FOREIGN PATENT DOCUMENTS

| | | |
|---|---|---|
| CN | 1977762 B | 10/2010 |
| JP | 05-192299 A | 8/1993 |
| JP | 07-194546 A | 8/1995 |
| JP | 11-028189 A | 2/1999 |
| JP | 11-070080 A | 3/1999 |
| JP | H11-070074 A | 3/1999 |
| JP | 2003-093348 A | 4/2003 |
| JP | 2005-013473 A | 1/2005 |
| JP | 2010-148586 A | 7/2010 |
| JP | 2012-120890 A | 6/2012 |

* cited by examiner

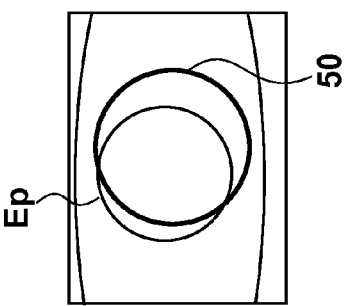
FIG. 3A
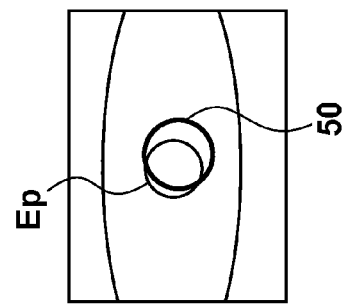
FIG. 3B
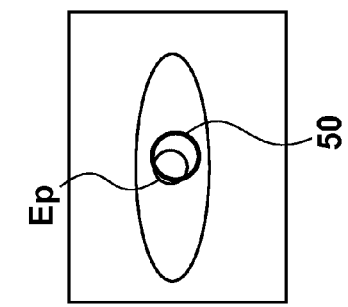
FIG. 3C
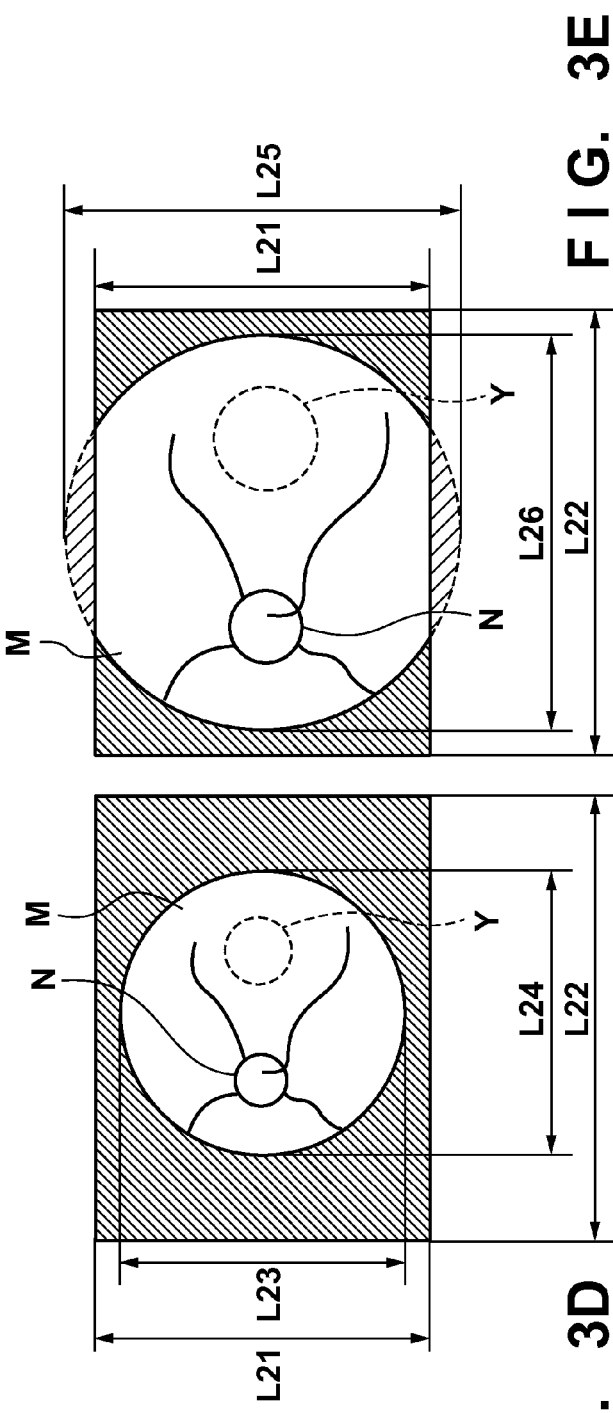
FIG. 3D
FIG. 3E

FIG. 4A

| OBSERVATION MODE | DISPLAY MAGNIFICATION |
|---|---|
| ANTERIOR OCULAR OBSERVATION | ×2.0 |
| FUNDUS OBSERVATION | ×1.3 |
| ANTERIOR OCULAR IMAGING | ×1.0 |

FIG. 4B

| OPERATION | DISPLAY MAGNIFICATION |
|---|---|
| FOCUSING | ×2.0 |
| MAIN BODY MOVEMENT | ×1.0 |

FIG. 4C

| OBSERVATION MODE | DISPLAY MAGNIFICATION |
|---|---|
| ANTERIOR OCULAR OBSERVATION | ×1.0 |
| FUNDUS OBSERVATION | ×1.0 |
| ANTERIOR OCULAR IMAGING | ×1.0 |

FIG. 7C

Table 71:

| OBSERVATION MODE | DISPLAY 61 | DISPLAY 62 |
|---|---|---|
| ANTERIOR OCULAR OBSERVATION | ×4.0 | ×1.0 |
| ANTERIOR OCULAR OBSERVATION | ×2.0 | ×1.0 |

FIG. 7D

Table 72:

| OBSERVATION MODE | DISPLAY 65 | DISPLAY 66 | DISPLAY 67 | DISPLAY 68 |
|---|---|---|---|---|
| FUNDUS OBSERVATION | ×1.0 | ×1.3 | ×1.3 | ×1.3 |
| FUNDUS OBSERVATION | ×1.3 | ×1.3 | ×1.3 | ×1.3 |

OPHTHALMIC APPARATUS, IMAGE PROCESSING METHOD, AND STORAGE MEDIUM

BACKGROUND OF THE INVENTION

Field of the Invention

The present invention relates to an ophthalmic apparatus, an image processing method, and a storage medium.

Description of the Related Art

When using a conventional fundus camera, an examiner aligns the eye to be examined while observing an image of the eye on a display unit. When performing this alignment, the examiner performs alignment first while observing an anterior ocular segment image of the eye to be examined and the pupil in a wide field of view and then performs alignment while observing a fundus image of the eye.

There is known a fundus camera which electronically enlarges an anterior ocular segment image to enlarge and observe an observation image when an operator observes an anterior ocular segment image (Japanese Patent Laid-Open No. 7-194546). In addition, as cameras for observing a fundus image, there are known a fundus camera (Japanese Patent Laid-Open No. 5-192299) which enlarges and displays the fundus image captured by a built-in monitor and a fundus camera (Japanese Patent Laid-Open No. 2010-148586) which enlarges and displays the central portion of a fundus image in focus operation for focusing.

There has recently been proposed a technique of mounting a general-purpose digital camera in the optical system of a fundus camera, capturing a fundus image by the image sensor mounted in the general-purpose digital camera, and displaying a captured fundus image on the display unit of the general-purpose digital camera. In addition, there is known a fundus camera among recent fundus cameras which is capable of imaging the anterior ocular segment as well as capturing a fundus image.

The display units mounted in many such general-purpose digital cameras, however, have small sizes. It is therefore difficult to align the eye to be examined by using an image of the eye displayed on the display unit of such a general-purpose digital camera. Deciding, in particular, a display magnification so as to facilitate alignment at the time of observation of a fundus image will reduce the size of an image at the time of anterior ocular observation depending on the optical design and the like. This makes it difficult to improve the accuracy of alignment of the anterior ocular segment. For this reason, switching from the anterior ocular observation mode to the fundus image observation mode will display a fundus image at a shifted position. It therefore takes much time to perform alignment.

Assume that the optical display magnification is increased at the time of anterior ocular observation to solve the above problem. In this case, since an image of the anterior ocular segment is displayed in a narrow range, it is difficult to grasp the positions of the anterior ocular segment and pupil of the eye to be examined, resulting in an increase in time to align the anterior ocular segment. In addition, increasing the optical display magnification will narrow the imaging range for the anterior ocular segment.

The present invention has been made in consideration of the above problem and provides a technique capable of facilitating alignment and focus adjustment with respect to the eye to be examined by displaying an observation image at a proper display magnification for each observation state.

SUMMARY OF THE INVENTION

According to one aspect of the present invention, there is provided a ophthalmic apparatus comprising: an imaging unit configured to obtain, through a photographing optical system, an image of an eye to be examined which is illuminated with illumination light from an observation light source of an illumination optical system; a display unit configured to display the image obtained by the imaging unit; and an image processing unit configured to display an image of the eye on the display unit at a display magnification corresponding to an observation portion of the eye or a display magnification corresponding to operation of the imaging unit.

According to another aspect of the present invention, there is provided an image processing method for an ophthalmic apparatus including an imaging unit configured to obtain, through a photographing optical system, an image of an eye to be examined which is illuminated with illumination light from an observation light source of an illumination optical system and a display unit configured to display the image obtained by the imaging unit, the method comprising an image processing step of displaying an image of the eye on the display unit at a display magnification corresponding to an observation portion of the eye or a display magnification corresponding to operation of the imaging unit.

According to the present invention, it is possible to facilitate alignment and focus adjustment with respect to the eye to be examined by displaying an observation image at a proper display magnification for each observation state.

Further features of the present invention will become apparent from the following description of exemplary embodiments (with reference to the attached drawings).

BRIEF DESCRIPTION OF THE DRAWINGS

FIGS. 3A to 3C are views each showing a display example of an observation image of an anterior ocular segment;

FIGS. 3D and 3E are views each showing a display example of an observation image of a fundus;

FIGS. 4A to 4C are views showing setting examples of display magnifications;

FIGS. 7C and 7D are views exemplarily showing display magnification settings.

DESCRIPTION OF THE EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

First Embodiment

Figure 1:
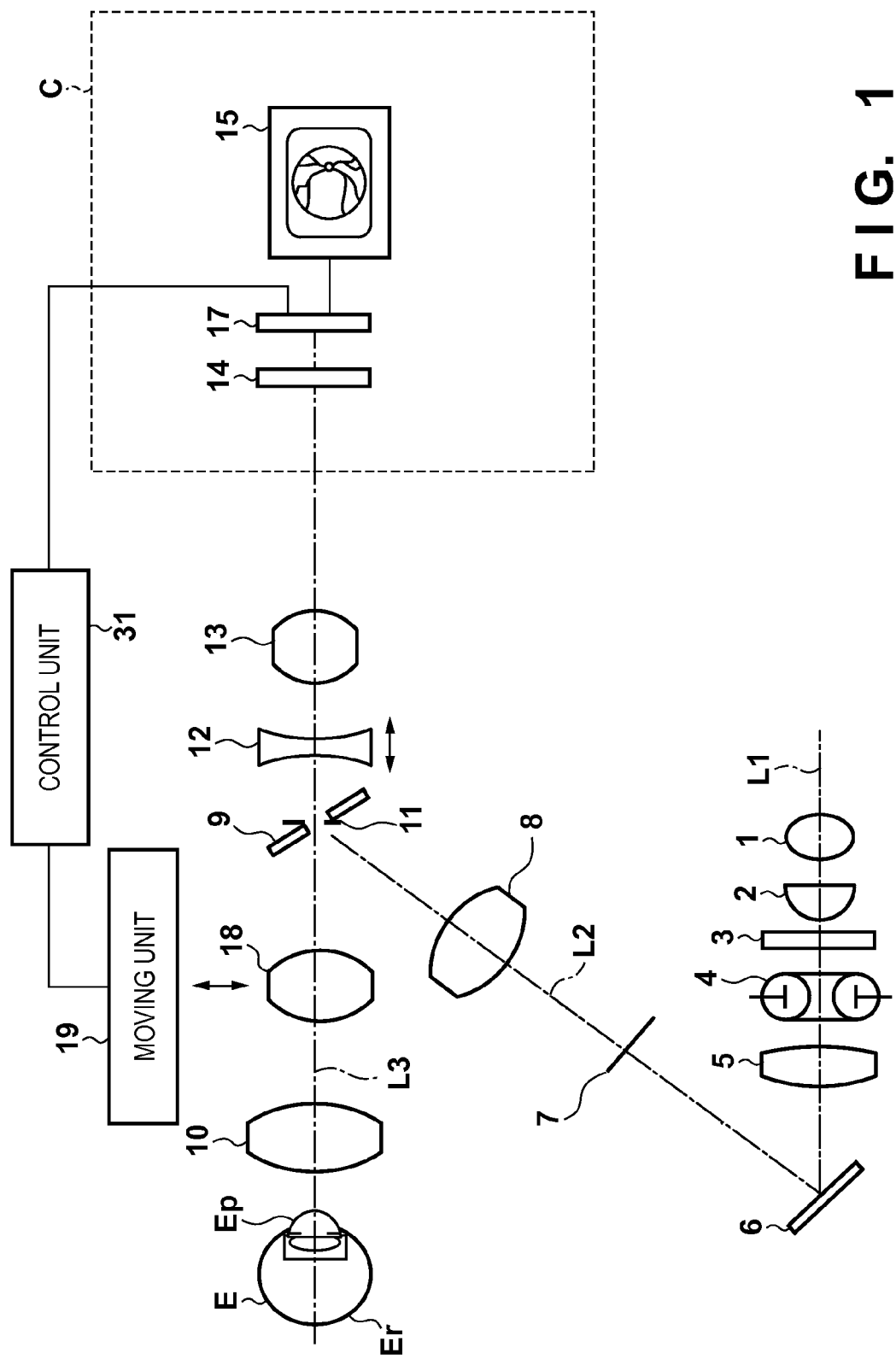
FIG. 1 is a view exemplarily showing the arrangement of a fundus camera according to an embodiment.

FIG. 1 is a view exemplarily showing the arrangement of a fundus camera as an ophthalmic apparatus according to an embodiment of the present invention. An observation light source 1 which emits infrared light, a condenser lens 2, a filter 3 which transmits infrared light and cuts off visible light, an imaging light source 4 such as a strobe, a lens 5, and a mirror 6 are arranged on an optical path L1. A ring stop 7 having a ring-like aperture, a relay lens 8, and a perforated mirror 9 having an aperture in the central portion are arranged on an optical path L2 in the reflection direction of the mirror 6.

An objective lens 10 is placed on an optical path L3 in the reflecting direction of the perforated mirror 9 so as to face the eye E. An imaging stop 11 is placed on the optical path L3 in the hole portion of the perforated mirror 9. A focusing lens 12 which adjusts the focus by moving on the optical path L3 and an imaging lens 13 are arranged on the optical path L3. FIG. 1 shows a state in which an anterior ocular lens 18 is inserted between the objective lens 10 and the perforated mirror 9 on the optical path L3. The anterior ocular lens 18 is connected to a moving unit 19 which moves under the control of the focusing processing unit 31. The moving unit 19 allows the anterior ocular lens 18 to move onto the optical path L3 or move away (retreat) from the optical path L3.

An imaging unit (image sensor 14) serving both for moving image observation and still image capturing is arranged in a fundus camera C ahead of the imaging lens 13. The image sensor 14 is connected to an image processing unit 17. A display unit 15 is connected to the image processing unit 17. The image processing unit 17 processes an image signal from the image sensor 14. The image processing unit 17 processes an image of the eye to be examined so as to display it on the display unit 15 at a display magnification corresponding to an observation portion of the eye or a display magnification corresponding to the operation of the fundus camera. The image processing unit 17 outputs the processed data to a control unit 31 and the display unit 15 (monitor). The display unit 15 displays an observation image of the eye which is processed by the image processing unit 17. Note that the fundus camera C (including the image sensor 14 and the display unit 15) may be detachable with respect to the photographing optical system.

Figure 2:
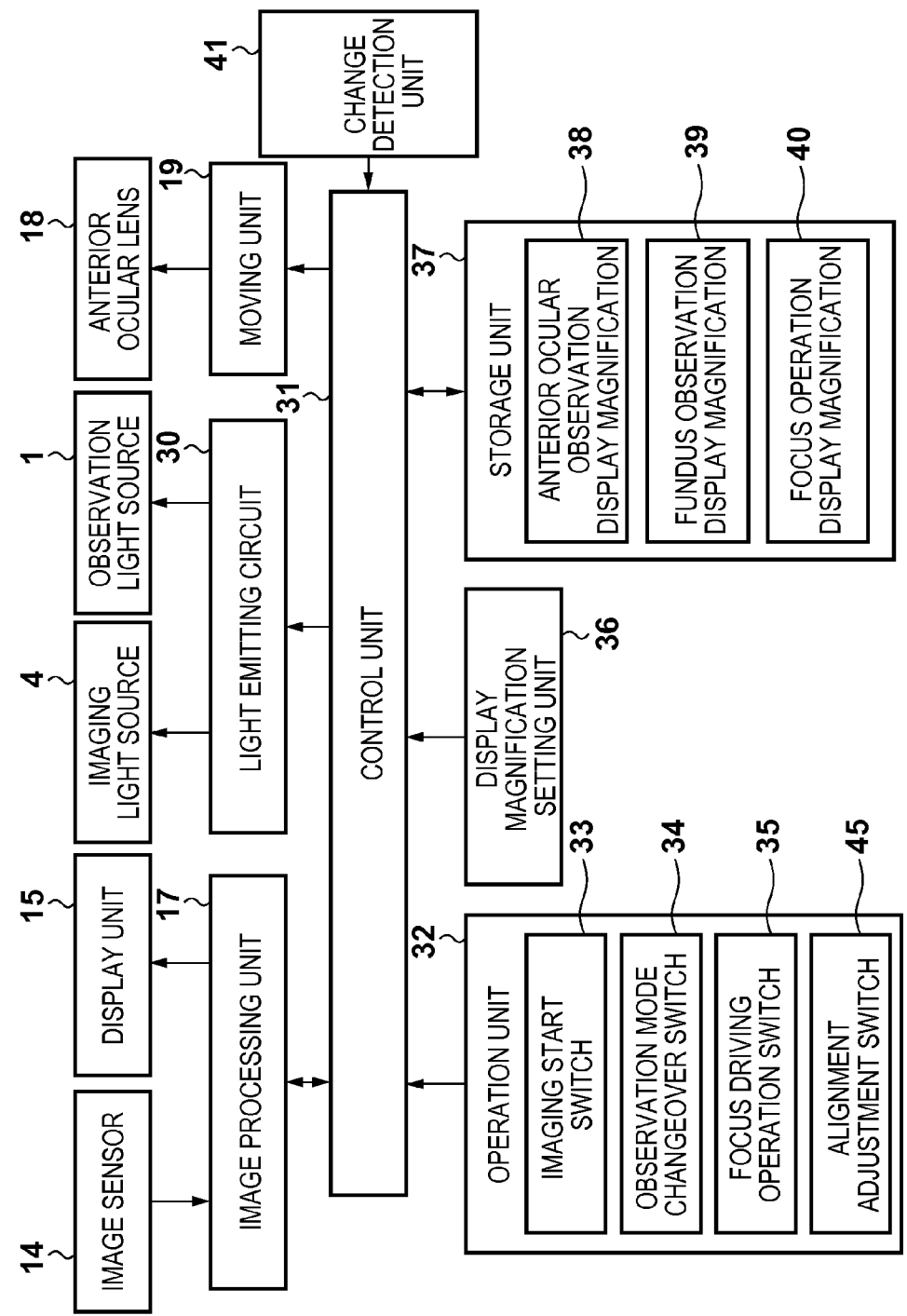
FIG. 2 is a block diagram showing the functional arrangement of a fundus camera according to the first embodiment.

FIG. 2 is a block diagram showing the functional arrangement of the fundus camera. The control unit 31 controls the overall operation of the fundus camera. The moving unit 19 which moves the anterior ocular lens 18, the image processing unit 17, a light emitting circuit 30, a change detection unit 41, a storage unit 37, a display magnification setting unit 36, and an operation unit 32 are connected to the control unit 31. The operation unit 32 includes an imaging start switch 33, an observation mode changeover switch 34, a focus driving operation switch 35 for driving the focusing lens 12, and an alignment adjustment switch 45 for performing relative alignment between the eye E and the fundus camera. Information concerning an anterior ocular observation display magnification 38 and a fundus observation display magnification 39 is set as display magnifications corresponding to an observation portion of the eye to be examined in the storage unit 37. In addition, information concerning a focus operation display magnification 40 at the time of focusing operation is set in the storage unit 37 as a display magnification corresponding to the operation of the imaging unit (image sensor 14).

The change detection unit 41 detects a change in observation portion or a change in the operation of the fundus camera. When the change detection unit 41 detects a change in observation portion of the fundus camera (for example, a change from anterior ocular observation to fundus observation), the display magnification setting unit 36 obtains display magnification information corresponding to the changed observation portion from the storage unit 37, and sets it as the display magnification of the display unit 15 in the image processing unit 17. The image processing unit 17 generates a mask having an aperture at a position corresponding to the central portion which defines a predetermined angle of view of a fundus Er in accordance with the display magnification set by the display magnification setting unit 36.

When the change detection unit 41 detects a change in the operation of the fundus camera, the display magnification setting unit 36 obtains display magnification information corresponding to the change in operation from the storage unit 37, and sets it as the display magnification of the display unit 15 in the image processing unit 17. The image processing unit 17 displays the image of the eye on the display unit 15 in accordance with the display magnification set by the display magnification setting unit 36.

An imaging light source 4 and an observation light source 1 are connected to the light emitting circuit 30. The control unit 31 controls light amount adjustment and ON/OFF operation of the observation light source 1 and light amount adjustment and ON/OFF operation of the imaging light source 4 via the light emitting circuit 30.

Before performing fundus observation, the operator performs anterior ocular observation for aligning the anterior ocular segment (pupil Ep) of the eye to be examined with a designated position. In general, when performing anterior ocular observation, it is necessary to let the object sit and find the eye to be examined. The operator therefore finds the eye within the display range of the display unit 15 and performs alignment while moving the main body of the fundus camera upward, downward, leftward, rightward, forward, and backward. In this case, it is important to quickly find the eye within the display range of the display unit 15 in consideration of a reduction in burden on the object and efficient imaging. It is therefore necessary to also display the periphery of the eye on the display unit 15.

When the operator operates the observation mode changeover switch 34, the control unit 31 controls the moving unit 19 so as to move the anterior ocular lens 18 onto the optical path L3. The control unit 31 then turns on the observation light source 1 by controlling the light emitting circuit 30. When the light emitting circuit 30 turns on the observation light source 1, the emitted light passes through the optical paths L1, L2, and L3 of the illumination optical system extending from the observation light source 1 to the anterior ocular lens 18 and the objective lens 10 and illuminates the anterior ocular segment of the eye E. An image of the anterior ocular segment illuminated with this observation light passes through the objective lens 10, the anterior ocular lens 18, the perforated mirror 9, the focusing lens 12, and the imaging lens 13 on the optical path L3, as an imaging optical system, and reaches the image sensor 14 in the fundus camera C. At this time, the image processing unit 17 processes the image of the anterior ocular segment obtained by the image sensor 14, and displays the image on the display unit 15 at the display magnification corresponding to the anterior ocular observation mode.

When performing fundus observation after aligning the anterior ocular segment with a designated position by anterior ocular observation, the operator operates the focus driving operation switch 35 to perform precise alignment (fundus alignment) and focus adjustment with respect to the eye E for fundus observation. When the light emitting circuit 30 turns on the observation light source 1, the emitted infrared observation light passes through the optical paths L1, L2, and L3 of the illumination optical system extending from the observation light source 1 to the objective lens 10 and illuminates the fundus Er through the pupil Ep of the eye E. An image of the fundus Er illuminated with this observation light passes through the optical path L3 including the objective lens 10 and the perforated mirror 9 and reaches the image sensor 14 in the fundus camera C. The image processing unit 17 processes the fundus image of infrared light obtained by the image sensor 14 and displays the processed image on the display unit 15 at a display magnification corresponding to the observation mode for the fundus as an observation portion. Although this embodiment commonly uses the image sensor 14 for fundus observation and anterior ocular observation, it is possible to use different image sensors for anterior ocular observation and fundus observation.

FIGS. 3A, 3B, and 3C exemplarily show observation images of the anterior ocular segment (pupil Ep) at display magnifications of X1.0, X2.0, and X4.0, respectively. When performing anterior ocular observation, the operator concentrically aligns the anterior ocular segment (pupil Ep) with an alignment mark 50 (alignment index). When changing the display magnification, the display magnification setting unit 36 displays the alignment mark 50 upon changing its size in accordance with the display magnification. The operator operates the alignment adjustment switch 45 while seeing the image displayed on the display unit 15. The operator concentrically aligns the anterior ocular segment (pupil Ep) as an observation portion with the alignment mark 50 by moving the main body of the fundus camera upward, downward, leftward, rightward, forward, and backward, thereby relatively aligning the eye E with the fundus camera.

The display magnification shown in FIG. 3A allows the operator to widely observe the anterior ocular segment. This makes it easy to find the eye to be examined. However, since the pupil Ep is displayed in a small size, it may be difficult to accurately align the pupil Ep if the display unit 15 is small in size. If the accuracy of alignment of the pupil Ep is low, switching to the fundus observation mode will make it difficult to see a fundus image, resulting in a deterioration in the efficiency of alignment at the time of fundus observation. The display magnification shown in FIG. 3C can display the pupil Ep in a large size and hence can improve the accuracy of alignment of the pupil. However, this narrows the observation area of the anterior ocular segment and hence will make it difficult to find the eye to be examined. If, therefore, it is difficult to align the pupil Ep at the display magnifications in FIGS. 3A and 3C, it is possible to set a display magnification between the display magnifications in FIGS. 3A and 3C, as shown in FIG. 3B. Setting a proper display magnification in accordance with the size of the display unit 15 will improve the operability in concentrically aligning the pupil Ep with the alignment mark 50 at the time of anterior ocular observation.

FIGS. 3D and 3E exemplarily show fundus observation images when the display unit 15 is small in size. FIGS. 3D and 3E respectively show examples of images at display magnifications of X1.0 and X1.3. Note that the image processing unit 17 displays, on the display unit 15, the image obtained by electronically combining a fundus image with a mask having an aperture at a position corresponding to the central portion which defines a predetermined angle with respect to the fundus Er. The image processing unit 17 enlarges the fundus image and the aperture portion of the mask in accordance with the display magnification and displays them on the display unit 15.

Consider a case in which the apparatus performs imaging centered on the posterior pole at which a macula lutea region N and a papilla region Y have a uniform positional relationship. In general, the operator performs alignment at the time of fundus observation while seeing the positional relationship between the macula lutea region, the papilla region, and main arteries and veins. Referring to FIG. 3E, the fundus image is displayed with chipped portions relative to the angle of view at which imaging is performed at the time of fundus observation. Only the hatched portions in FIG. 3E, excluding the macula lutea region N, the papilla region Y, and the main arteries and veins, are omitted. This has no influence on alignment. Even with the small-size display unit 15, therefore, it is possible to easily perform alignment (fundus alignment) and focus adjustment.

Referring to FIGS. 3D and 3E, reference symbol L21 denotes the length of the display area of the display unit 15 in the transverse direction; L22, the length of the display area of the display unit 15 in the longitudinal direction; L23, the length of an aperture M of the mask in the L21 direction at a display magnification of X1.0; L24, the length of the aperture M of the mask in the L22 direction at a display magnification of X1.0; L25, the length of the aperture M of the mask in the L21 direction at a display magnification of X1.3; and L26, the length of the aperture M of the mask in the L22 direction at a display magnification of X1.3.

Although FIG. 3E exemplifies the case with a display magnification of X1.3, the present invention is not limited to this. It is possible to decide an enlargement magnification by using the lengths L21, L22, L25, and L26. It is possible to set any magnification at which the aperture M of the mask is not chipped in the longitudinal direction of the display area in the display range of the display unit 15 and is chipped in the transverse direction. For example, it is possible to set any magnification satisfying the relationships of L22≥L26, L22≈L26, and L21≤L25. If the display unit 15 is small in size, it is possible to set the display magnification shown in FIG. 3E. When performing focusing with focus adjustment, the target portion for focusing may be enlarged to facilitate visualization. This embodiment has exemplified the arrangement configured to store display magnification settings in the storage unit 37. However, the display magnification setting unit 36 may calculate (obtain) a magnification that satisfies relationships of L22 L26, L22≈L26, and L21≤L25 and set the calculated magnification as the display magnification of the display unit 15. The display magnification setting unit 36 may obtain display magnification information from an external information processing apparatus via a network.

FIG. 4A shows an example of a display magnification setting for each observation mode when the display unit 15 is small in size. The "anterior ocular imaging" is the imaging mode for imaging the anterior ocular segment. FIG. 4B shows an example of display magnification settings at which the display unit 15 displays when the operator operates the fundus camera. Referring to FIG. 4B, when, for example, the operator adjusts the focus of the fundus camera, a display magnification of X2.0 is set. When the operator moves the main body, a display magnification of X1.0 is set. In this case, to "move the main body" is to move the fundus camera upward, downward, leftward, rightward, forward, and backward. Referring to FIG. 4B, when the operator moves the main body of the fundus camera upward, downward, leftward, rightward, forward, and backward, the display magnification is commonly set to X1.0. However, the present invention is not limited to this. For example, it is possible to set a display magnification for each moving direction, including the upward/downward direction, the leftward/rightward direction, and the forward/backward direction. In addition, when using a fundus camera having a variable magnification mode and small pupil modes, it is possible to set display magnifications for the respective operations.

Figure 5:
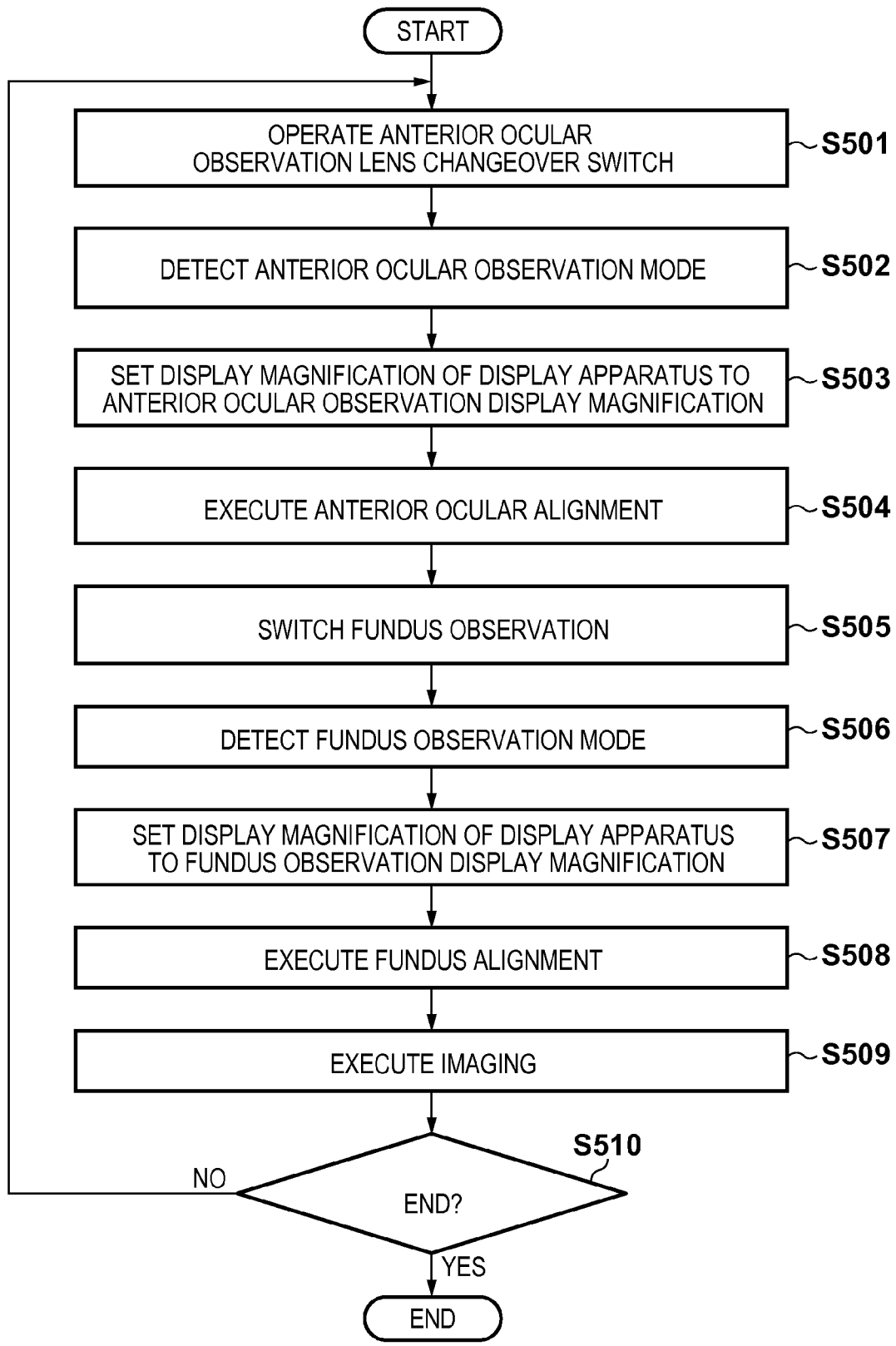
FIG. 5 is a flowchart for explaining a procedure for observation mode switching processing and display magnification switching processing.

FIG. 5 is a flowchart for explaining a procedure for observation mode (observation portion) switching processing and display magnification switching processing in the fundus camera. Assume in the following description that the display magnifications shown in FIGS. 4A and 4B are set. First of all, in step S501, the operator starts to examine the eye to be examined by operating the observation mode changeover switch 34. Note that the control unit 31 of the fundus camera may perform switching operation of the observation mode changeover switch 34 instead of the operator.

In step S502, when the change detection unit 41 detects that the observation mode has been switched to the anterior ocular observation mode upon operation of the observation mode changeover switch 34, the control unit 31 controls the moving unit 19 to move the anterior ocular lens 18 onto the optical path L3.

In step S503, the display magnification setting unit 36 obtains the display magnification for the anterior ocular observation mode from the storage unit 37 and sets it as the display magnification of the display unit 15 in the image processing unit 17. This makes the display unit 15 display an observation image of the anterior ocular segment at a display magnification of X2.0, as shown in FIG. 3B.

In step S504, the operator executes alignment of the anterior ocular segment. The operator operates the alignment adjustment switch 45 while seeing the image displayed on the display unit 15 to move the main body of the fundus camera upward, downward, leftward, rightward, forward, and backward, thereby relatively aligning the eye E with the fundus camera. At this time, when the operator moves the main body of the fundus camera, the control unit 31 controls the display unit 15 to display at a display magnification of X1.0, as shown in FIG. 3A. Changing the display magnification from X2.0 to X1.0 allows the operator to widely observe the anterior ocular segment. This makes it possible to easily find the eye to be examined and quickly perform alignment.

After the completion of the movement of the main body of the fundus camera, the control unit 31 performs control to display at a display magnification of X2.0 by returning the display magnification of the display unit 15 to that shown in FIG. 3B. When the operator has manually changed the display magnification, the display magnification setting unit 36 can control the display magnification setting so as to display at the manually set display magnification until the observation mode is changed.

When the alignment of the pupil is complete by alignment of the anterior ocular segment, the operator operates the observation mode changeover switch 34 in step S505 to switch the observation mode from the anterior ocular observation mode to the fundus observation mode. In this case, the control unit 31 controls the moving unit 19 to move (retract) the anterior ocular lens 18 away from the optical path L3 in accordance with the operation of the observation mode changeover switch 34. Note that the control unit 31 may automatically detect the alignment of the pupil and switch to the fundus observation mode instead of the operation by the operator.

In step S506, the change detection unit 41 detects that the observation mode has been switched from the anterior ocular observation mode to the fundus observation mode.

In step S507, the display magnification setting unit 36 obtains the display magnification of the fundus observation mode from the storage unit 37, and sets it as the display magnification of the display unit 15 in the image processing unit 17. This causes the display unit 15 to display an image of the fundus at a display magnification of X1.3, as shown in FIG. 3E. At this display magnification, the display unit 15 displays an enlarged view of the main part of the fundus which is required for alignment and focus adjustment without displaying any portion which can be omitted without causing any trouble in alignment (fundus alignment) and focus adjustment. The display at this display magnification can facilitate alignment and focus adjustment even with the small-size display unit 15.

In step S508, the operator executes fundus alignment. The operator operates the focus driving operation switch 35 to perform alignment and focus adjustment with respect to the fundus while seeing the image displayed on the display unit 15. When the focusing operation is complete, the display magnification setting unit 36 returns the display magnification of the display unit 15 to the original display magnification (a display magnification of X1.0). Returning the display magnification of the display unit 15 to the original display magnification (a display magnification of X1.0) (FIG. 3D) allows the operator to check whether there is no imaging error for a fundus image at a predetermined angle of view.

In step S509, the operator operates the imaging start switch 33 to capture a fundus image. Note that the captured image is displayed at the display magnification shown in FIG. 3D to check whether there is no imaging error with respect to the fundus image at a predetermined angle of view.

In step S510, the operator determines whether to terminate the processing. When, for example, imaging only one eye in one examination, the apparatus terminates the processing (YES in step S510). When imaging the left and right eyes or starting the next examination (NO in step S510), the process returns to step S501 to repeat similar processing. In this case, the control unit 31 can control the fundus camera to automatically return to the anterior ocular observation mode for the other eye upon completion of imaging of one eye.

According to this embodiment, it is possible to easily perform alignment and focus adjustment with respect to the eye to be examined even with a small-size display unit by setting a display magnification for each observation state of the eye.

Second Embodiment

Figure 6:
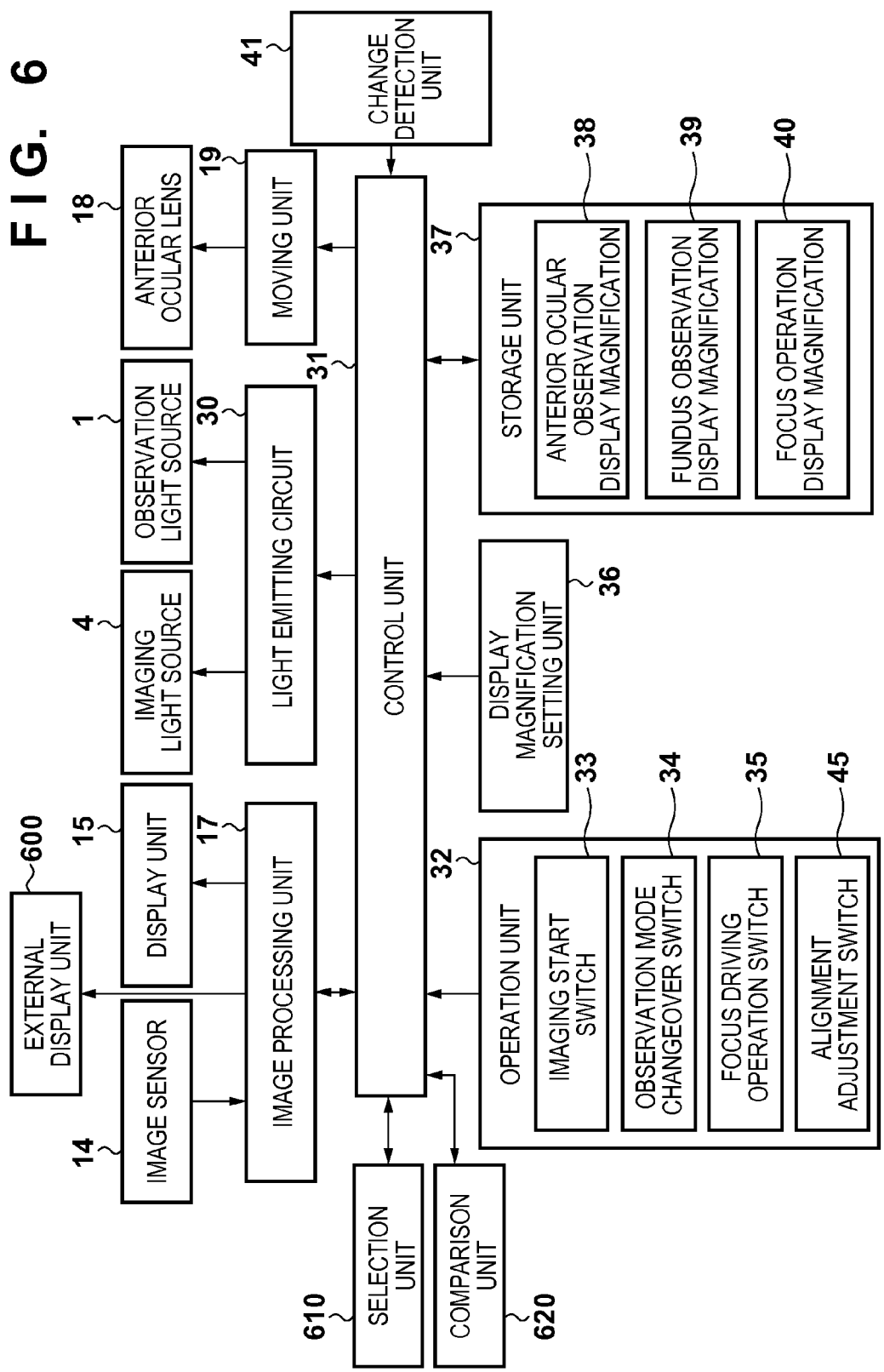
FIG. 6 is a block diagram showing the functional arrangement of a fundus camera according to the second embodiment.

This embodiment will exemplify an arrangement in which an external display unit 600 different from a display unit 15 is connected to an image processing unit 17. FIG. 6 is a block diagram showing the functional arrangement of a fundus camera according to the second embodiment of the present invention and apparatus connected to the camera. The same reference numerals as in FIG. 2 denote the same components in FIG. 6, and a description of them will be omitted. The functional arrangement shown in FIG. 6 is the same as that shown in FIG. 2 except that it additionally includes the external display unit 600, a selection unit 610, and a comparison unit 620.

The selection unit 610 and the comparison unit 620 are connected to a control unit 31. The external display unit 600 is connected to the control unit 31 via the image processing unit 17. Upon detecting the connection of the external display unit 600 by connection detection processing, the control unit 31 notifies the comparison unit 620 and a display magnification setting unit 36 of the corresponding information. The comparison unit 620 obtains information representing the size of the display area of the newly connected external display unit 600 via the image processing unit 17 and the control unit 31. The comparison unit 620 also obtains information representing the size of the display area of the display unit 15 via the image processing unit 17 and the control unit 31 and compares the size of the display area of the external display unit 600 with that of the display unit 15. The comparison unit 620 notifies the control unit 31 of the comparison result on this magnitude relationship and the information representing the size of the display area.

The selection unit 610 can select which one of the display unit 15 and the external display unit 600 should be used for alignment and focus adjustment by using the comparison result on the magnitude relationship. Note that this selection may be based on an input from the operator via the operation unit 32.

If the external display unit 600 has a display area larger than that of the display unit 15, it is possible to observe the anterior ocular segment and fundus of the eye to be examined on the display unit larger than the display unit 15 by externally connecting the external display unit 600 to the fundus camera. In this case, when displaying an image on the external display unit 600, it is possible to observe the image at the entire angle of view by displaying the image without enlargement. Therefore, displaying the image in a wide range will facilitate finding the eye to be examined at the time of anterior ocular observation. Since the size of the display area is sufficiently large, the operator can easily align the pupil. At the time of fundus observation, since it is possible to observe the entire angle of view, it is easy to perform alignment and focus adjustment. For this reason, the selection unit 610 can select a display unit having a large display area.

The display magnification setting unit 36 obtains information representing the size of the display area of the display unit selected by the selection unit 610 from the control unit 31. The display magnification setting unit 36 obtains information representing a display magnification corresponding to the selected display unit from the storage unit 37 by using the obtained information representing the size of the display area, and sets the information in the image processing unit 17.

Enlarged display like that described in the first embodiment is the display operation which facilitates seeing the main part of the eye to be examined on a small-size display unit. When displaying an image on the external display unit 600 having a large display area, there is no need to perform enlarged display by setting a display magnification exceeding X1.0. In this case, the display magnification setting unit 36 obtains information representing the display magnification (X1.0) shown in FIG. 4C from the storage unit 37 and sets the information as the display magnification of the external display unit 600 in the image processing unit 17. The image processing unit 17 generates a mask having an aperture at a position corresponding to the central portion which defines a predetermined angle of view with respect to a fundus Er in accordance with the display magnification set by the display magnification setting unit 36.

When a plurality of display units are connected to the fundus camera via the image processing unit 17, the selection unit 610 selects which one of the display unit 15 and the external display unit 600 should be used for alignment and focus adjustment. The display magnification setting unit 36 obtains information representing the size of the display area from the display unit selected by the selection unit 610 via the image processing unit 17 and the control unit 31. The display magnification setting unit 36 obtains information representing a display magnification corresponding to the selected display unit from the storage unit 37 by using the obtained information representing the size of the display area, and sets the obtained information as the display magnification of the selected display unit in the image processing unit 17. A display magnification corresponding to the selected display unit is automatically set by the processing by the selection unit 610, the comparison unit 620, and the display magnification setting unit 36. This further improves the operability.

Third Embodiment

Figure 7A:
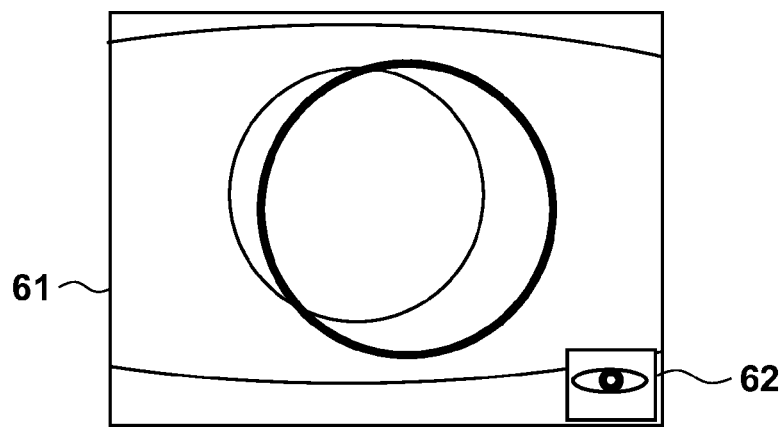
FIGS. 7A and 7B are views each showing a display example of the observation image obtained by a fundus camera according to the third embodiment.

This embodiment will exemplify an arrangement configured to display a plurality of images in the display area of a display unit when displaying the image on the display unit having the large display area. FIG. 7A is a view exemplarily showing the display of a plurality of observation images of the anterior ocular segment. A display 61 is an enlarged display of a observation image of the anterior ocular segment at a display magnification of X4.0. The display 61 corresponds to FIG. 3C. A display 62 is a display of the anterior ocular segment in a wide range at a display magnification of X1.0. The display 62 corresponds to FIG. 3A.

In this embodiment, an anterior ocular observation display magnification 38 is set as a display magnification for each of partial display areas (displays 61 and 62) in the display area of the display unit. FIG. 7C is a view exemplarily showing display magnification settings corresponding to the displays 61 and 62. Display magnification settings are merely examples, and various magnification settings can be set. When displaying an image like that shown in FIG. 7A, a display magnification setting unit 36 obtains information representing a display magnification like that of anterior ocular observation 71 in FIG. 7C from a storage unit 37, and sets it as the display magnification of the display unit in an image processing unit 17.

The display like that shown in FIG. 7A allows the operator to roughly align the anterior ocular segment with respect to the overall eye to be examined while seeing the display 62 and then accurately align the anterior ocular segment of the eye while seeing the display 61. Displaying images in partial areas (displays 61 and 62) of the display area upon setting different display magnifications can achieve both good viewability and high convenience and perform alignment optimal for anterior ocular observation. It is possible to change the display sizes of the displays 61 and 62 by changing the display magnification settings in FIG. 7C. Even if the display unit is changed, it is possible to perform optimal alignment and focus adjustment with respect to the anterior ocular segment in accordance with the size of the display area of the display unit.

Figure 7B:
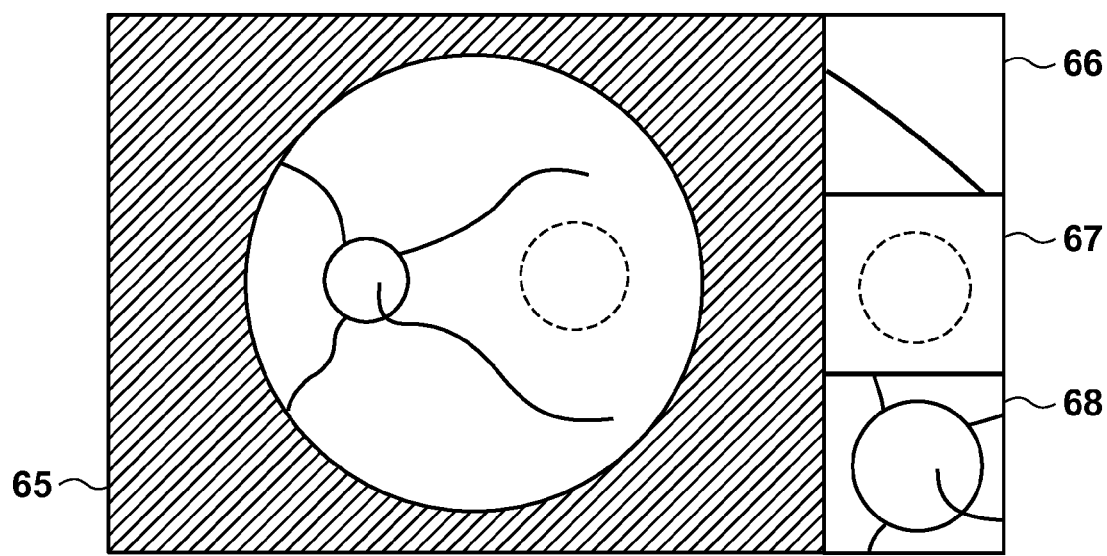

FIG. 7B is a view exemplarily showing a display of a plurality of observation images of the fundus. A display 65 is an entire angle-of-view display of the fundus. This display corresponds to FIG. 3D. A display 66 is an enlarged display of arteries or veins of the fundus. A display 67 is an enlarged display of the macula lutea region of the fundus. A display

68 is an enlarged display of the papilla region of the fundus. Displays 66, 67, and 68 are displays of partial images of the respective region of the fundus of the enlarged displays in FIG. 3E.

In this embodiment, a fundus observation display magnification 39 is set as a display magnification for each of partial display areas (displays 65 to 68) in the display area of the display unit. FIG. 7D is a view exemplarily showing display magnification settings corresponding to the displays 65 to 68 in the fundus observation mode. Display magnification settings are merely examples, and various magnification settings can be set. When displaying an image like that shown in FIG. 7B, a display magnification setting unit 36 obtains information representing a display magnification like that of fundus observation 72 in FIG. 7D from a storage unit 37, and sets it as the display magnification of the display unit in an image processing unit 17.

Performing display like that shown in FIG. 7B allows the operator to perform alignment of the fundus by using the entire angle-of-view display of the fundus of the display 65 and can perform focus adjustment and check while seeing an enlarged display of each region of the fundus. The operator need not enlarge an image of each region by operating an operation unit 32 to check whether each region of the fundus is in focus, and can simultaneously check focusing with respect to the macula lutea region, papilla region, arteries, and veins of the fundus. It is possible to change the display sizes of the displays 65 to 68 by, for example, changing the display magnification settings in FIG. 7D. Even if the display unit is changed, it is possible to perform optimal alignment and focus adjustment with respect to the fundus in accordance with the size of the display area of the display unit.

Each embodiment described above has exemplified the arrangement of the fundus camera as an ophthalmic apparatus. However, the scope of the present invention is not limited to the fundus camera. For example, even if the present invention is applied to an OCT (Optical Coherence Tomography) and SLO (Scanning Laser Ophthalmoscope), it is possible to display an observation image of the eye to be examined at a proper display magnification for each observation state. This can facilitate alignment and focus adjustment with respect to the eye to be examined.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-247751, filed Nov. 9, 2012, which is hereby incorporated by reference herein in its entirety.

What is claimed is:

1. An ophthalmic apparatus comprising:
an imaging unit configured to obtain, through a photographing optical system, an image of an eye to be examined which is illuminated with illumination light from an observation light source of an illumination optical system;
a detection unit configured to detect, as an observation portion of the eye, an anterior ocular segment of the eye or a fundus of the eye; and
an image processing unit configured to display an image of the eye on a display unit at a display magnification corresponding to the detected observation portion.

2. The apparatus according to claim 1, further comprising:
a setting unit configured to obtain information of a display magnification corresponding to the observation portion,
wherein the image processing unit displays an image of the eye on the display unit at the display magnification based on the information obtained by the setting unit.

3. The apparatus according to claim 2, further comprising:
a connection detection unit configured to detect connection of an external display unit different from the display unit;
a comparison unit configured to compare information representing a size of a display area of the external display unit with information representing a size of a display area of the display unit when connection of the external display unit is detected; and
a selection unit configured to select one of the display unit and the external display unit, which has a larger display area, based on a comparison result obtained by the comparison unit,
wherein, when the external display unit is selected, (1) the setting unit obtains information of a display magnification corresponding to the external display unit and (2) the image processing unit displays an image of the eye at a display magnification based on the information obtained by the setting unit.

4. The apparatus according to claim 3, wherein, when the selection unit selects the external display unit, the image processing unit displays, on the external display unit, an image of the anterior ocular segment which is enlarged at a display magnification corresponding to observation of the anterior ocular segment and an image of the anterior ocular segment at an entire angle of view which is not enlarged at the display magnification.

5. The apparatus according to claim 3, wherein, when the selection unit selects the external display unit, the image processing unit displays, on the external display unit, an image obtained by combining an image of the fundus with a mask having an aperture at a position corresponding to a central portion of the fundus and a partial image of the fundus.

6. The apparatus according to claim 2, wherein, when operation of the apparatus is changed by an operation unit, (1) the setting unit obtains information of a display magnification corresponding to the changed operation, and (2) the image processing unit displays an image of the eye on the display unit at a display magnification set by the setting unit while the changed operation continues.

7. The apparatus according to claim 6, wherein the image processing unit displays an image of the eye on the display unit at a display magnification before the operation of the apparatus is changed by an operation unit after completion of the operation of the apparatus.

8. The apparatus according to claim 1, wherein when an anterior ocular segment of the eye is observed, the image processing unit displays an image of the anterior ocular segment and an alignment index for aligning the anterior ocular segment with a designated position on the display unit at a display magnification corresponding to observation of the anterior ocular segment.

9. The apparatus according to claim 1, wherein when a fundus of the eye is observed, the image processing unit displays, on the display unit, an image of the fundus at a display magnification corresponding to observation of the fundus upon combining the image with a mask having an aperture at a position corresponding to a central portion of the fundus.

10. The apparatus according to claim 1, wherein the imaging unit and the display unit are detachable from the photographing optical system.

11. The apparatus according to claim 1, wherein the image processing unit displays an image of the eye on the display unit at a display magnification in observation of an anterior ocular segment of the eye that is different from a display magnification in observation of a fundus of the eye.

12. The apparatus according to claim 11, wherein the image processing unit displays the image of the eye on the display unit at a display magnification in observation of the anterior ocular segment of the eye that is larger than a display magnification in observation of the fundus of the eye.

13. The apparatus according to claim 1, further comprising:
a setting unit configured to obtain information of a display magnification corresponding to the detected observation portion,
wherein the image processing unit displays an image of the eye on the display unit at the display magnification based on the information obtained by the setting unit.

14. The apparatus according to claim 1, further comprising an observation mode changeover switch configured to switch between (1) an anterior ocular observation mode to observe the anterior ocular segment and (2) a fundus observation mode to observe the fundus,
wherein the detection unit detects the observation portion in accordance with an operation of the observation mode changeover switch.

15. The apparatus according to claim 1, wherein the detection unit detects, as the observation portion, the anterior ocular segment in a case where alignment between the anterior ocular segment and the apparatus is completed while displaying an image of the anterior ocular segment on the display unit at a display magnification corresponding to observation of the anterior ocular segment.

16. An image processing method for an ophthalmic apparatus including an imaging unit configured to obtain, through a photographing optical system, an image of an eye to be examined which is illuminated with illumination light from an observation light source of an illumination optical system, the method comprising:
a detection step of detecting, as an observation portion of the eye, an anterior ocular segment of the eye or a fundus of the eye; and
an image processing step of displaying an image of the eye on a display unit at a display magnification corresponding to the detected observation portion.

17. The method according to claim 16, wherein the an image of the eye is displayed on a display unit at a display magnification in observation of the anterior ocular segment of the eye that is different from a display magnification in observation of the fundus of the eye.

18. The method according to claim 17, wherein the image of the eye is displayed on the display unit at a display magnification in observation of the anterior ocular segment of the eye that is larger than a display magnification in observation of the fundus of the eye.

19. A non-transitory computer-readable storage medium storing a program for causing a computer to serve as each unit of an ophthalmic apparatus, wherein the apparatus comprises:
an imaging unit configured to obtain, through a photographing optical system, an image of an eye to be examined which is illuminated with illumination light from an observation light source of an illumination optical system; and
a detection unit configured to detect, as an observation portion of the eye, an anterior ocular segment of the eye or a fundus of the eye; and
an image processing unit configured to display an image of the eye on a display unit at a display magnification corresponding to the detected observation portion.

20. An ophthalmic apparatus comprising:
an imaging unit configured to obtain, through a photographing optical system, an image of an eye to be examined which is illuminated with illumination light from an observation light source of an illumination optical system;
a detection unit configured to detect an operation for adjusting of an optical element of the apparatus;
a setting unit configured to obtain information of a display magnification corresponding to the operation for adjusting of an optical element of the apparatus; and
an image processing unit configured to display an image of the eye on a display unit at the display magnification based on the obtained information.

21. The apparatus according to claim 20, wherein, when an anterior ocular segment of the eye is observed, the image processing unit displays an image of the anterior ocular segment and an alignment index for aligning the anterior ocular segment with a designated position on the display unit at a display magnification corresponding to observation of the anterior ocular segment.

22. The apparatus according to claim 20, wherein, when a fundus of the eye is observed, the image processing unit displays, on the display unit, an image of the fundus at a display magnification corresponding to observation of the fundus upon combining the image with a mask having an aperture at a position corresponding to a central portion of the fundus.

23. The apparatus according to claim 20, wherein, when operation of the apparatus is changed by an operation unit, (1) the setting unit obtains information of a display magnification corresponding to the changed operation, and (2) the image processing unit displays an image of the eye on the display unit at a display magnification set by the setting unit while the changed operation continues.

24. The apparatus according to claim 23, wherein the image processing unit displays an image of the eye on the display unit at a display magnification before the operation of the apparatus is changed by an operation unit after completion of the operation.

25. The apparatus according to claim 20, wherein the imaging unit and the display unit are detachable from the photographing optical system.

26. The apparatus according to claim 20, further comprising:

a connection detection unit configured to detect connection of an external display unit different from the display unit;

a comparison unit configured to compare information representing a size of a display area of the external display unit with information representing a size of a display area of the display unit when connection of the external display unit is detected; and a selection unit configured to select one of the display unit and the external display unit, which has a larger display area, based on a comparison result obtained by the comparison unit, wherein, when the external display unit is selected, (1) the setting unit obtains information of a display magnification corresponding to the external display unit and (2) the image processing unit displays an image of the eye at a display magnification based on the information obtained by the setting unit.

27. The apparatus according to claim 26, wherein, when the selection unit selects the external display unit, the image processing unit displays, on the external display unit, (1) an image of the anterior ocular segment which is enlarged at a display magnification corresponding to observation of the anterior ocular segment and (2) an image of the anterior ocular segment at an entire angle of view which is not enlarged at the display magnification.

28. The apparatus according to claim 26, wherein, when the selection unit selects the external display unit, the image processing unit displays, on the external display unit, an image obtained by combining an image of the fundus with a mask having an aperture at a position corresponding to a central portion of the fundus and a partial image of the fundus.

29. The apparatus according to claim 20, the image processing unit displays an image of the eye on the display unit at a display magnification in an alignment operation that is different from a display magnification in a focusing operation.

30. The apparatus according to claim 29, wherein the image processing unit displays the image of the eye on the display unit at a display magnification in the focusing operation that is larger than a display magnification in the alignment operation.

31. The apparatus according to claim 20, further comprising:

a setting unit configured to obtain information of a display magnification corresponding to an operation for adjusting of an optical element of the apparatus, wherein the image processing unit displays an image of the eye on the display unit at the display magnification based on the information obtained by the setting unit.

32. A non-transitory computer-readable storage medium storing a program for causing a computer to serve as each unit of an ophthalmic apparatus, wherein the apparatus comprises:

an imaging unit configured to obtain, through a photographing optical system, an image of an eye to be examined which is illuminated with illumination light from an observation light source of an illumination optical system;

a detection unit configured to detect an operation for adjusting of an optical element of the apparatus;

a setting unit configured to obtain information of a display magnification corresponding to the operation for adjusting of an optical element of the apparatus; and an image processing unit configured to display an image of the eye on a display unit at the display magnification based on the obtained information.

33. An image processing method for an ophthalmic apparatus including an imaging unit configured to obtain, through a photographing optical system, an image of an eye to be examined which is illuminated with illumination light from an observation light source of an illumination optical system, the method comprising:

a detection step of detecting an operation for adjusting of an optical element of the apparatus;

a setting step of obtaining information of a display magnification corresponding to the operation for adjusting of an optical element of the apparatus; and an image processing step of displaying an image of the eye on a display unit at the display magnification based on the obtained information.

* * * * *